(12) United States Patent
Goodman et al.

(10) Patent No.: US 11,874,269 B2
(45) Date of Patent: Jan. 16, 2024

(54) TEST PAD AND SYSTEM

(71) Applicants: Bonnie Goodman, Acton, CA (US);
Jeff Goodman, Acton, CA (US)

(72) Inventors: Bonnie Goodman, Acton, CA (US);
Jeff Goodman, Acton, CA (US)

( * ) Notice: Subject to any disclaimer, the term of this patent is extended or adjusted under 35 U.S.C. 154(b) by 0 days.

(21) Appl. No.: 16/896,102

(22) Filed: Jun. 8, 2020

(65) Prior Publication Data

US 2020/0386737 A1    Dec. 10, 2020

Related U.S. Application Data

(60) Provisional application No. 62/858,256, filed on Jun. 6, 2019.

(51) Int. Cl.
*G01N 33/493*    (2006.01)
*A61B 10/00*    (2006.01)
*G01N 33/84*    (2006.01)

(52) U.S. Cl.
CPC .......... *G01N 33/493* (2013.01); *A61B 10/007* (2013.01); *G01N 33/84* (2013.01)

(58) Field of Classification Search
CPC ..... G01N 33/493; G01N 33/84; A61B 10/007
See application file for complete search history.

(56) References Cited

U.S. PATENT DOCUMENTS

| | | | | |
|---|---|---|---|---|
| 2,785,057 | A * | 3/1957 | Schwab | G01N 33/525 422/408 |
| 6,572,822 | B2 * | 6/2003 | Jurik | G01N 33/66 422/423 |
| 2008/0103414 | A1 * | 5/2008 | Song | G01N 33/558 600/573 |
| 2009/0157024 | A1 * | 6/2009 | Song | G01N 21/80 604/361 |
| 2014/0261208 | A1 * | 9/2014 | Calimano | A01K 1/0107 119/161 |

FOREIGN PATENT DOCUMENTS

| | | | |
|---|---|---|---|
| CA | 2998020 A1 * | 8/2019 | |
| WO | WO-2017017676 A1 * | 2/2017 | ........... A01K 29/005 |

\* cited by examiner

*Primary Examiner* — Dennis White
(74) *Attorney, Agent, or Firm* — West & Associates, A PC; Stuart J. West; Charlotte Rodeen-Dickert

(57) ABSTRACT

A testing pad comprising a water-resistant base layer, a water-transmissive top layer coupled with said base layer, an hydrophilic intermediate layer contained between said top layer and said base layer, and a color-changing chemical reagent contained between said top layer and said base layer adapted an configured to allow an animal or person to urinate on the testing pad and the chemical reagent to present testing results related to the presence, absence and/or concentration of substances within the urine.

20 Claims, 6 Drawing Sheets

TEST PAD AND SYSTEM

CROSS-REFERENCE TO RELATED PATENT APPLICATIONS

This application claims the benefit of priority under 35 U.S.C. § 119 to prior filed and co-pending provisional patent application No. 62/858,256, filed by Bonnie Goodman and Jeff Goodman on Jun. 6, 2019, the entirety of which is hereby expressly incorporated herein by reference.

BACKGROUND

Technical Field

The present device relates to the field of medical testing and more specifically to the field of urine-based testing.

Background

Animals and people with diseases (chronic or otherwise) often require periodic urine testing to determine if treatment or medical intervention is required. Obtaining urine samples for testing from animals and some people can be difficult for the owner and/or service provider and sometimes traumatic to the animal or person as traditional methods of obtaining a urine sample from animal involve either trying to follow an animal around and catch urine in a receptacle as the animal urinates or with animals and people sometimes some form of medical procedure may be required if the animal or person is not cooperative.

What is needed is a simple an efficient way to allow an animal or person to void in a somewhat traditional manner without the need to "catch" the urine in a receptacle in order to perform further testing.

BRIEF DESCRIPTION OF THE DRAWINGS

Further details of the present device are explained with the help of the attached drawings in which.

DETAILED DESCRIPTION

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Figure 1:
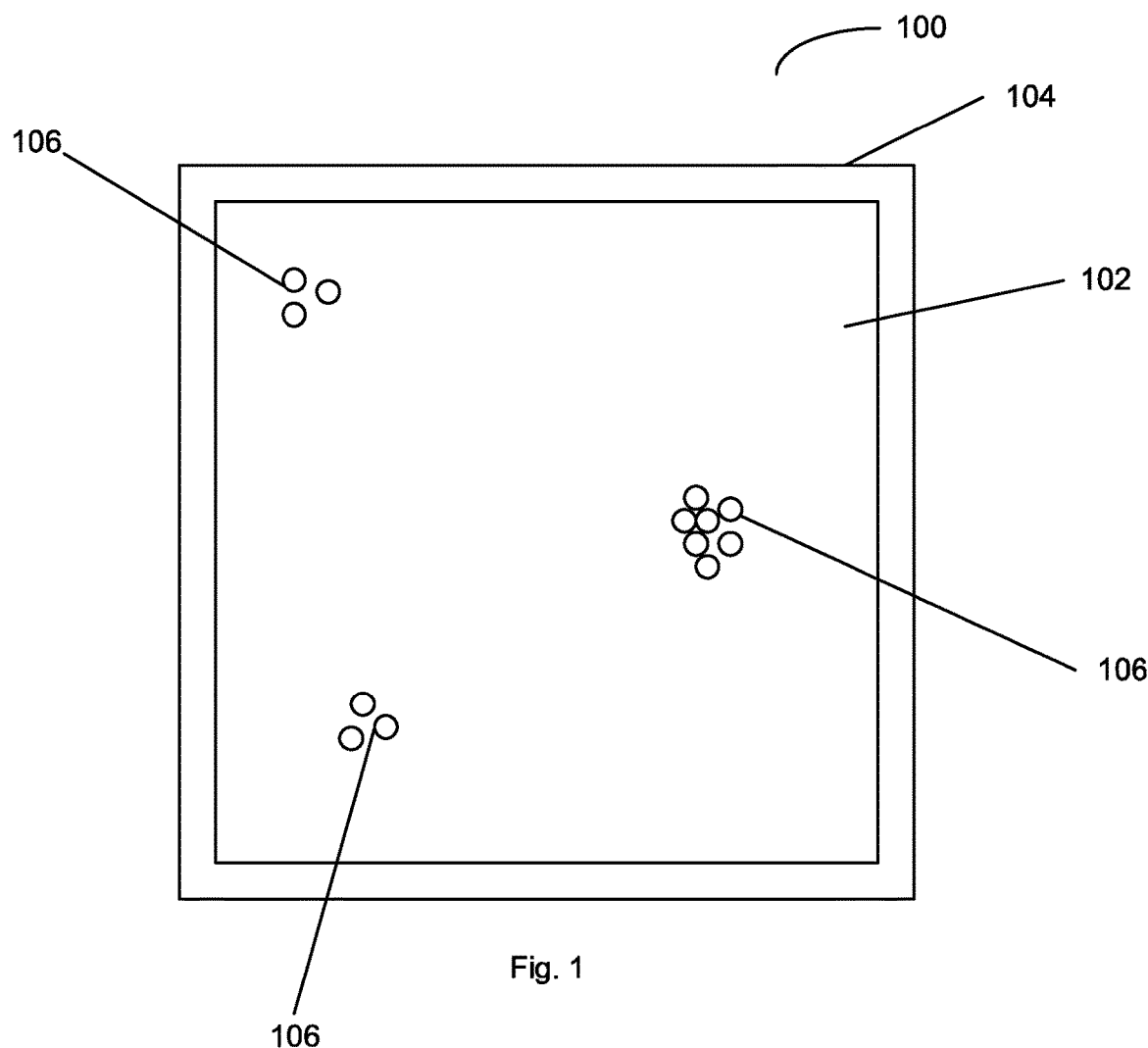
FIG. 1 depicts a top view of a testing pad.

FIG. 1 depicts a top view of a testing pad 100. In the embodiment depicted in FIG. 1, the testing pad 100 can comprise a central area 102 and a border area 104. The central area 102 can further comprise one or more and/or various testing areas 106 that comprise reagents configured to detect the presence, absence and/or indicate levels of one or more specific substances within urine that can be deposited on the testing pad 100. In some embodiments, the testing pad 100 or any component thereof can be impregnated or otherwise imbued with an attractant adapted and configured to encourage an animal to urinate on the testing pad 100.

In some embodiments, testing areas 106 can detect the presence or absence of one or more compounds, substances and/or chemicals within the urine. In some embodiments, the testing areas can provide visual test results for such things as the presence, absence, content or value of the following within the urine: blood, protein, pH, glucose, bilirubin, ketones, leukocytes, Nitrites, specific gravity, urobilinogen, progesterone and/or any other known, convenient and/or desired testing parameter. In some embodiments, the testing pad 100 can be specific to one of the testing parameters. However, in alternate embodiments, the testing pad 100 can have specific testing areas 106 that are specific to testing parameters and/or each testing area 106 can comprise regions and/or can test for a plurality of testing parameters.

In operation, a testing pad 100 can be placed on a surface, such as a floor or a bed. An animal or person can then urinate on the testing pad and the testing areas 106 can change color and/or otherwise visually indicate the presence, absence, value, content and/or level of specific substances within the urine of the animal or person. In some embodiments, the testing areas can detect the presence of ketones, glucose and/or proteins within the urine. However, in alternate embodiments any known, convenient and/or desired testing reagent can be housed within the testing area(s) 106 and the color of the testing area(s) 106 after urination can be used diagnostically to determine the presence, absence and/or level of any known, convenient and/or desired substance within the animal's or individual's urine.

Figure 2:
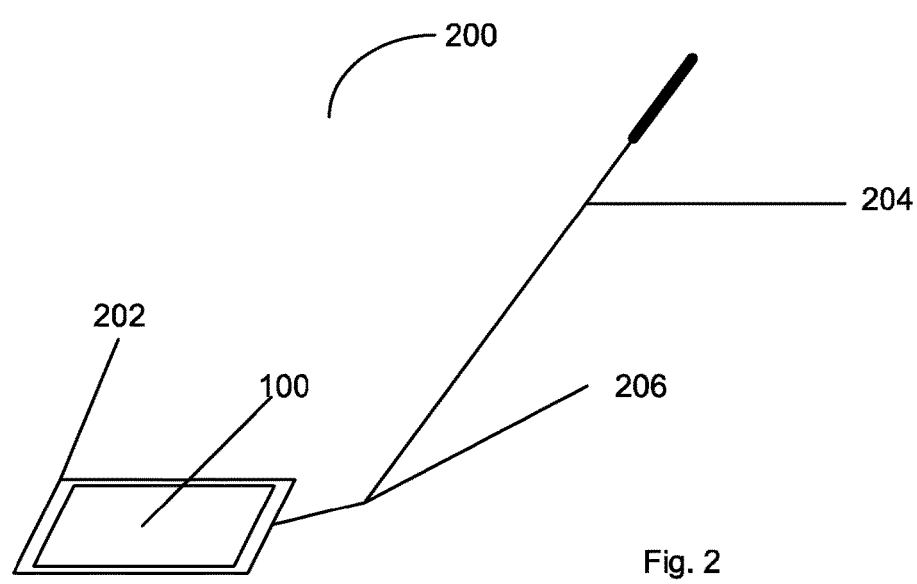
FIG. 2 depicts an isometric view of a testing pad in use on an adjustable pole.

FIG. 2 depicts an isometric view of a testing pad 100 in use on an adjustable pole 204. In some embodiments, the testing pad 100 can be used as a system 200 with a device to facilitate the placement of the testing pad 100 under an animal or person as the animal or person is urinating. In some embodiments, the device can comprise a substantially flat surface 202 coupled with a retractably pole 204 that can have a pivot mechanism 206 to facilitate sliding the testing pad 100 (on the flat surface 202 under an animal or person while the animal or person is in the process of urinating to obtain a sample of the urine on the testing pad 100.

Figure 3:
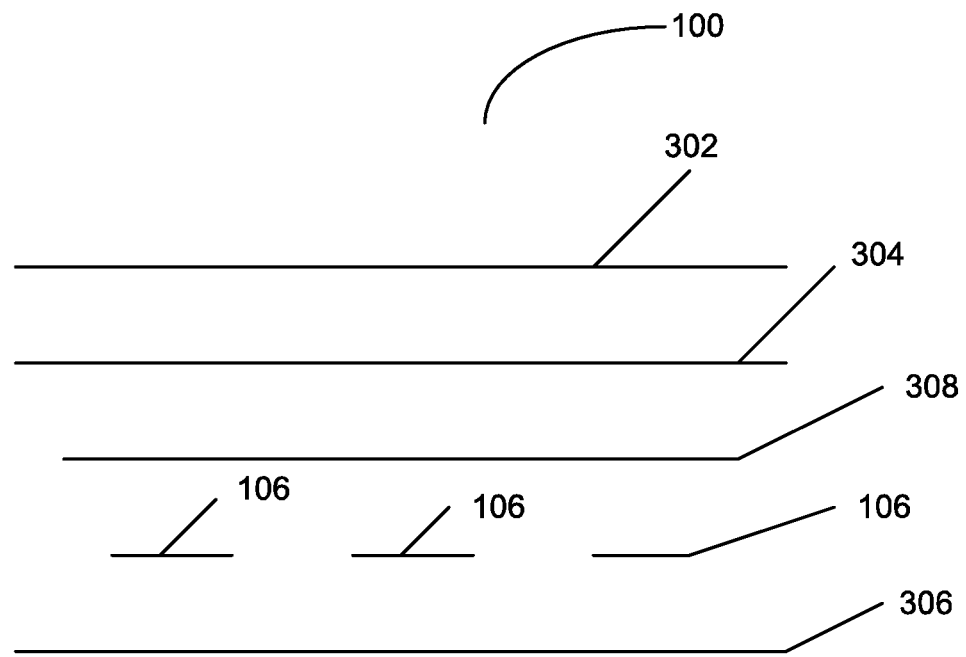
FIG. 3 depicts an exploded view of a cross-section of one embodiment of a testing pad.

FIG. 3 depicts an exploded view of a cross-section of one embodiment of a testing pad 100. The testing pad 100 can be comprised of various layers. In the embodiment depicted in FIG. 3, the testing pad 100 can comprise a top cover layer 302, a top liquid-permeable surface 304, a bottom liquid-barrier layer 306, an absorbent/disbursement layer 308 and testing area(s) 106. In the embodiment depicted in FIG. 3, the top cover layer 302 can be a protective layer adapted to keep the testing pad 100 surface substantially uncontaminated and/or sterile prior to use. However, in some embodiments, the top cover layer 302 may be absent.

In the embodiment depicted in FIG. 3, the top liquid-permeable layer can be comprised of a material adapted and configured to allow urine to easily pass through the layer and reach the absorbent/disbursement layer 308. The absorbent/disbursement layer 308 can be comprised of a material adapted and configured to distribute the urine across the testing pad 100 and allow the urine to be directed to or received by one or more testing areas 106 located below the absorbent/disbursement layer 308. Urine can then be contained or inhibited from reaching the surface on which the testing pad 100 rests by the bottom liquid barrier 306.

Figure 4:
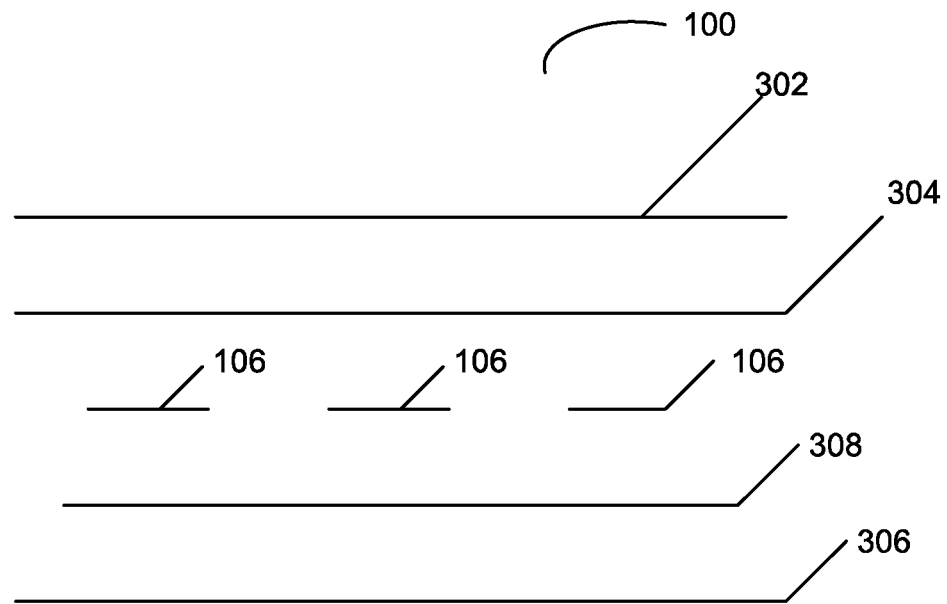
FIG. 4 depicts an exploded view of a cross-section of an alternate embodiment of a testing pad.

FIG. 4 depicts an alternate configuration of the layers of the testing pad 100 wherein the absorbent/disbursement layer is below the testing areas 106 and urine can reach the testing area(s) 106 either via direct urination of the animal or person from above the top surface and/or by the urine being delivered via the absorbent/disbursement layer 308 to the underside of the testing area(s) 106.

In some embodiments the testing pad 100 can be configured to test for a single substance and/or can be configured to test for a variety of substances. Additionally, in some embodiments the testing pad 100 can be provided pre-configured with testing area(s) 106 already filled with specific reagents to test for specific substances. However, in alternate embodiments, the testing area(s) 106 of the testing pad 100 can be user customizable and permit a user to insert various testing devices in the testing area(s) 106 such that the user can customize the testing pad 100 to test for any desired substances within the urine of the animal or person.

Figure 5:
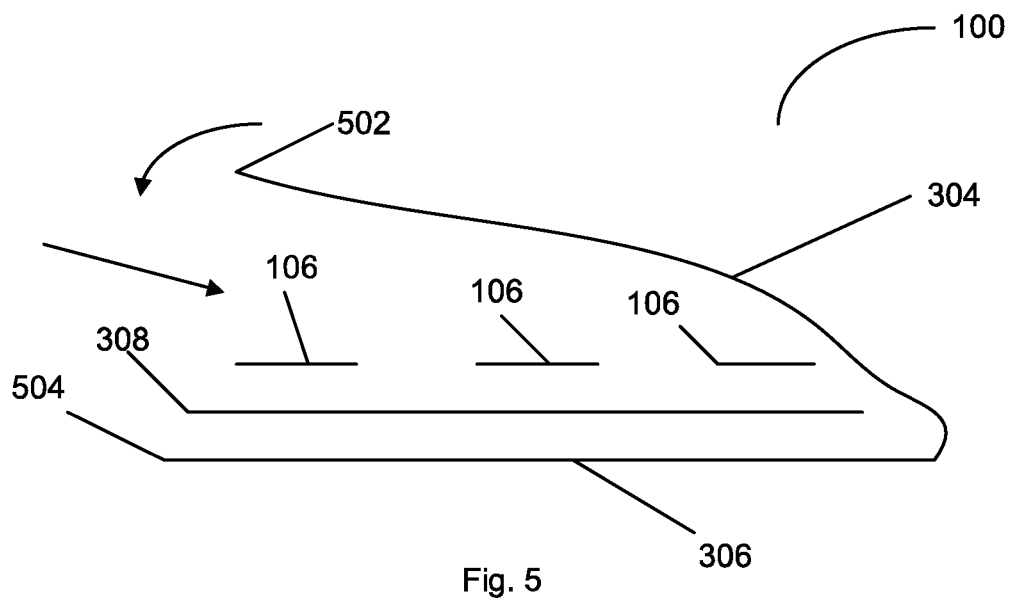
FIG. 5 depicts a cross-section of an alternate embodiment of a testing pad.
Figure 6:
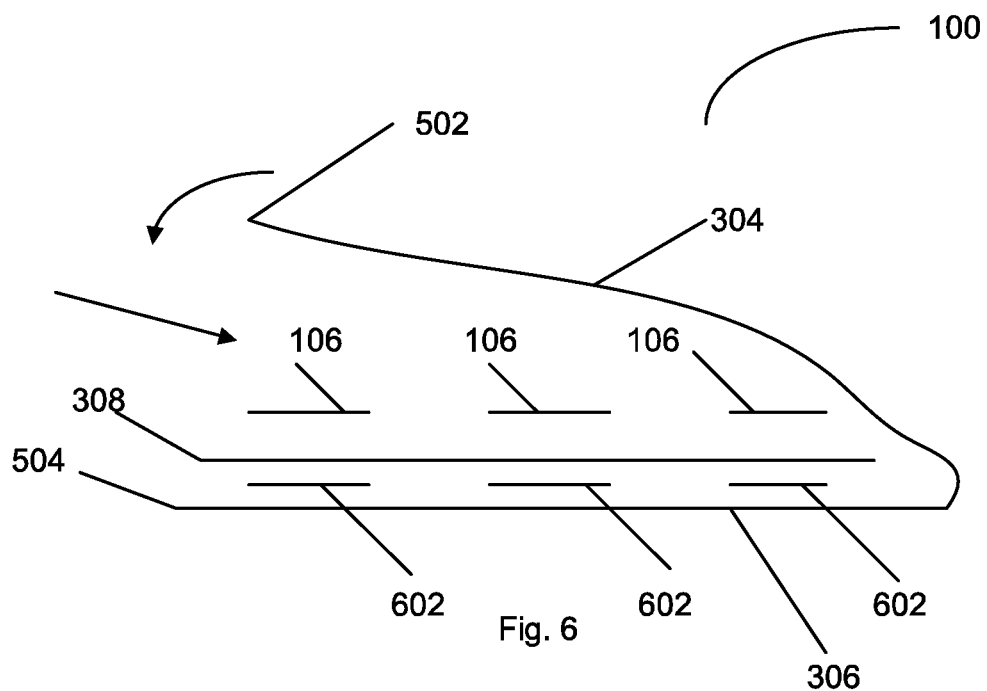
FIG. 6 depicts a cross-section of an alternate embodiment of a testing pad.

FIGS. 5 and 6 depict cross-sections of alternate embodiments of a testing pad 100. In the embodiment depicted in FIGS. 5 and 6, the test pad 100 may not be sealed at all edges thus permitting a user to selectively insert one or various testing strips within the test area(s) 106 and then seal a portion of or the balance of the perimeter of the testing pad via attachments 502 504 with the specific reagents contained within the testing pad 100, thereby allowing a user to customize the testing performed by the testing pad 100.

In some embodiments, as depicted in FIG. 6, the testing pad 100 can further comprise verification area(s) 602 located below the testing area(s) 106. Such verification areas 602 can provide a visual indication to the user that urine reached the testing area(s) 106 in sufficient quantity as to assure a valid test result.

Figure 7:
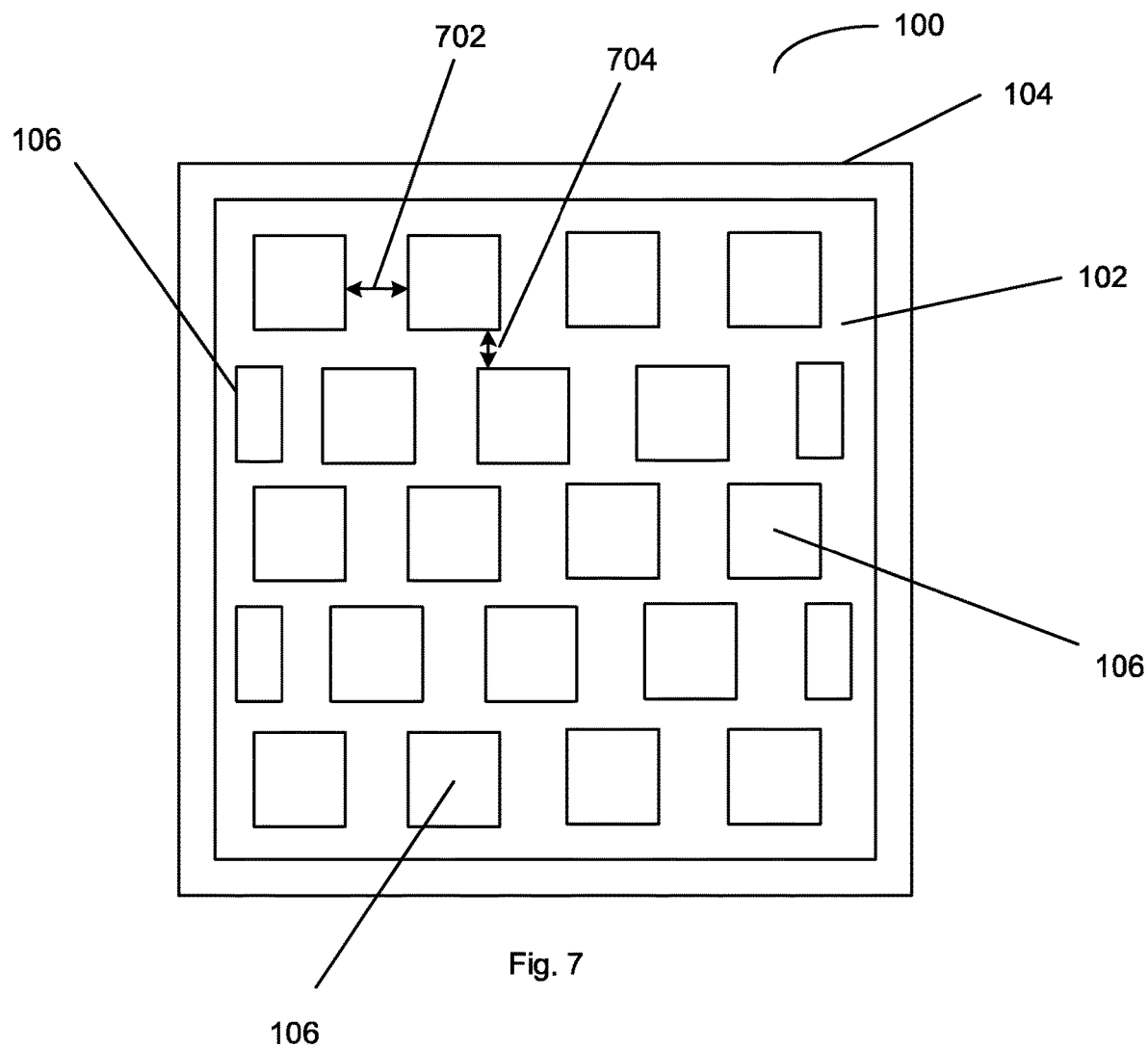
FIG. 7 depicts an alternate embodiment of a testing pad.
Figure 8:
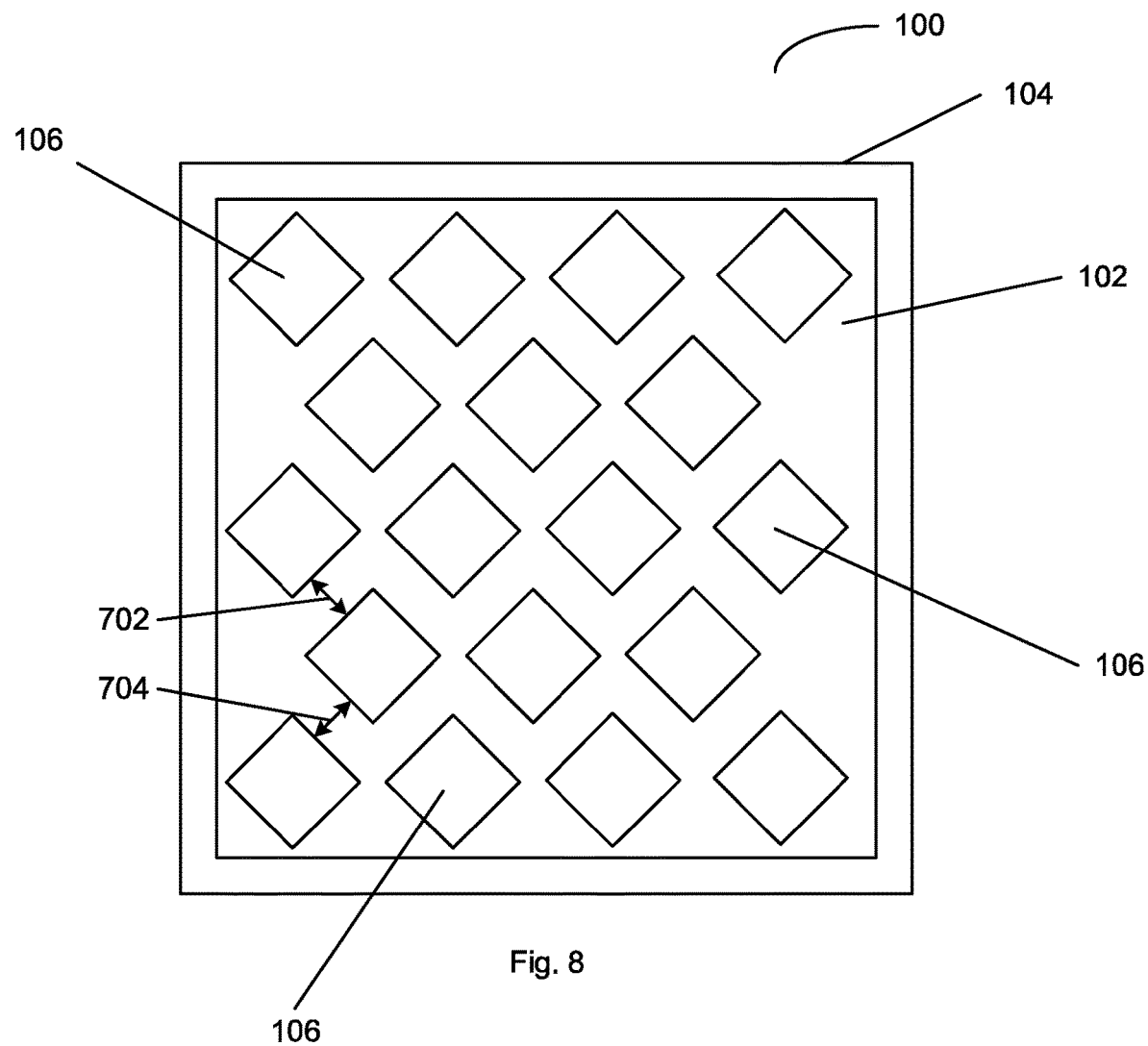
FIG. 8 depicts an alternate embodiment of a testing pad.
Figure 9:
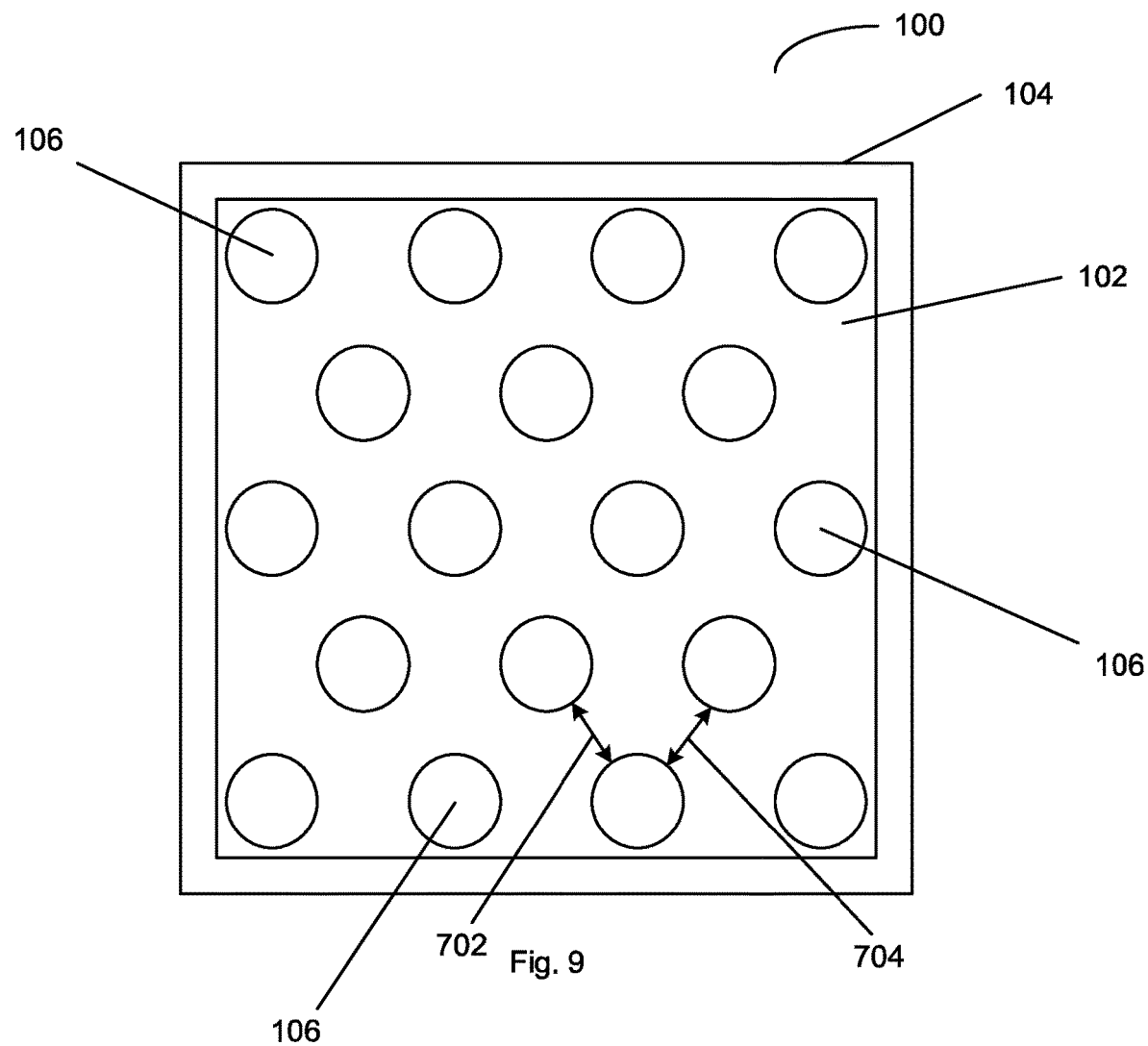
FIG. 9 depicts an alternate embodiment of a testing pad.

FIGS. 7-9 depict alternate embodiments of the testing pad 100. In the embodiment depicted in FIGS. 7-9 testing areas 106 which can comprise one or testing area 106, as previous described, which can test for the presence, absence, value, content and/or level of specific substances. Additionally, in some embodiments, testing pads 100 can have any known convenient and/or desired dimensions and can be sized for pets of various sizes and/or weights. Additionally, in some embodiments the testing areas 106 can have various and/or specific and/or desired spacing 702 704 of testing areas 106, in part due to the typical volume of urine usually voided by an animal of a given weight. By way of non-limiting example, in some embodiments in which an animal may be under approximately 23 lbs. or person under 40 pounds, the spacing 702 704 of testing areas 106 can be 1" or approximately 1" or less and/or in situations in which an animal weighs between 20 lbs. and 50 lbs. or person weights between 35 lbs. and 100 lbs., the spacing 702 704 of the testing areas 106 can be greater than 1" or approximately 1" and less than 2" or approximately 2". Additionally, by way of non-limiting example, in situations where an animal is large or extra large and weighs over 45 lbs. or over approximately 45 lbs. and/or a person weighs over 100 lbs., testing areas 106 can be spaced up to 5" or approximately 5" apart.

Finally, as depicted in FIGS. 7-9, testing areas can have any known convenient and/or desired shape and/or geometric configuration and can be positioned within the testing pad 100 at any known, convenient and/or desired locations and/or spacing (regular, periodic and/or irregular). That is, in some embodiments, the spacing 702 704 of the testing areas 106 can be different and/or random in one of more of spacing directions 702 704.

Although exemplary embodiments of the invention have been described in detail and in language specific to structural features and/or methodological acts above, it is to be understood that those skilled in the art will readily appreciate that many additional modifications are possible in the exemplary embodiments without materially departing from the novel teachings and advantages of the invention. Moreover, it is to be understood that the subject matter defined in the appended claims is not necessarily limited to the specific features or acts described above. Accordingly, these and all such modifications are intended to be included within the scope of this invention construed in breadth and scope in accordance with the appended claims.

What is claimed:

1. A testing pad comprising:
a bottom layer that is liquid impermeablei
a continuous top layer that is liquid permeable;
a perimeter edge;
at least two attachments;
wherein said continuous top layer is discontinuously coupled with said bottom layer along at least a portion of said perimeter edge such that said attachments seal a discontinuous portion of the perimeter edge with specific reagents contained within the testing pad, and covers a plurality of testing areas;
a top cover layer covering the entirety of said liquid permeable continuous top layer;
a hydrophilic intermediate layer contained between said continuous top layer and said bottom layer;
a plurality of color-changing chemical reagents contained within said testing areas between said continuous top layer and said bottom layer; and
an attractant adapted and configured to attract an animal to urinate on said pad;
wherein said plurality of said testing areas are distributed across an area defined by said continuous top layer.

2. The testing pad of claim 1, wherein said hydrophilic intermediate layer is adapted and configured to distribute liquid at least a portion of said hydrophilic intermediate layer.

3. The testing pad of claim 2, wherein said top layer is adapted and configured to be urine-transmissive to allow observation of a color change of said plurality of color-changing chemical reagents through said continuous top layer.

4. The testing pad of claim 3, wherein said continuous top layer is adapted and configured to permit at least one of blood, protein, glucose, bilirubin, ketones, leukocytes, nitrites, progesterone and urobilinogen to pass through said continuous top layer.

5. The testing pad of claim 3, wherein said color-changing layer is adapted and configured to provide a visual indication of at least one of the presence, absence value or level of at least one of blood, protein, pH, glucose, bilirubin, ketones, leukocytes, nitrites, specific gravity, progesterone and urobilinogen.

6. The testing pad of claim 4, wherein said color-changing layer is adapted and configured to provide a visual indication of the presence of at least one of blood, protein, glucose, bilirubin, ketones, leukocytes, nitrites, progesterone and urobilinogen.

7. The testing pad of claim 4, wherein said color-changing layer is adapted and configured to provide a visual indication of a level of at least one of blood, protein, pH, glucose, bilirubin, ketones, leukocytes, nitrites, specific gravity, progesterone and urobilinogen.

8. The testing pad of claim 4, wherein said color-changing layer is adapted and configured to provide a visual indication of a value associated with at least one of blood, protein, pH, glucose, bilirubin, ketones, leukocytes, nitrites, specific gravity, progesterone and urobilinogen.

9. The testing pad of claim 1, wherein said color-changing layer is adapted and configured to provide a visual indication of at least one of the presence, absence value or level of at least one of blood, protein, pH, glucose, bilirubin, ketones, leukocytes, nitrites, specific gravity, progesterone and urobilinogen.

10. The testing pad of claim 1, wherein said color-changing layer is adapted and configured to provide a visual indication of the presence of at least one of blood, protein, glucose, bilirubin, ketones, leukocytes, nitrites, progesterone, and urobilinogen.

11. The testing pad of claim 1, wherein said color-changing layer is adapted and configured to provide a visual indication of a level of at least one of blood, protein, pH, glucose, bilirubin, ketones, leukocytes, nitrites, specific gravity, progesterone and urobilinogen.

12. The testing pad of claim 1, wherein said color-changing layer is adapted and configured to provide a visual indication of a value associated with at least one of blood, protein, pH, glucose, bilirubin, ketones, leukocytes, nitrites, specific gravity, progesterone and urobilinogen.

13. The testing pad of claim 1, wherein said continuous top layer is adapted and configured to be urine-transmissive; and wherein at least one edge of said testing pad is unsealed to allow selective insertion of one or more of said color-changing chemical reagents within said testing areas between said continuous top layer and said bottom layer.

14. The testing pad of claim 13, wherein said color-changing layer is adapted and configured to provide a visual indication of at least one of the presence, absence value or level of at least one of blood, protein, pH, glucose, bilirubin, ketones, leukocytes, nitrites, specific gravity, progesterone and urobilinogen.

15. The testing pad of claim 13, wherein said color-changing layer is adapted and configured to provide a visual indication of the presence of at least one of blood, protein, glucose, bilirubin, ketones, leukocytes, nitrites, progesterone and urobilinogen.

16. The testing pad of claim 13, wherein said color-changing layer is adapted and configured to provide a visual indication of a level of at least one of blood, protein, pH, glucose, bilirubin, ketones, leukocytes, nitrites, specific gravity, progesterone and urobilinogen.

17. The testing pad of claim 13, wherein said color-changing layer is adapted and configured to provide a visual indication of a value associated with at least one of blood, protein, pH, glucose, bilirubin, ketones, leukocytes, nitrites, specific gravity, progesterone and urobilinogen.

18. The testing pad of claim 13, wherein said color-changing layer is adapted and configured to provide a visual indication of the presence of at least two of blood, protein, glucose, bilirubin, ketones, leukocytes, nitrites, progesterone and urobilinogen.

19. The testing pad of claim 13, wherein said color-changing layer is adapted and configured to provide a visual indication of levels of at least two of blood, protein, pH, glucose, bilirubin, ketones, leukocytes, nitrites, specific gravity, progesterone and urobilinogen.

20. The testing pad of claim 13, wherein said color-changing layer is adapted and configured to provide a visual indication of values associated with at least two of blood, protein, pH, glucose, bilirubin, ketones, leukocytes, nitrites, specific gravity, progesterone and urobilinogen.

* * * * *